United States Patent [19]
Fasano

[11] Patent Number: 6,114,964
[45] Date of Patent: Sep. 5, 2000

[54] SYSTEMS AND METHODS FOR FENCELINE AIR MONITORING OF AIRBORNE HAZARDOUS MATERIALS

[75] Inventor: Adam M. Fasano, Needham, Mass.

[73] Assignee: Geoenvironmental, Inc., Newton Upper Falls, Mass.

[21] Appl. No.: 09/143,699

[22] Filed: Aug. 28, 1998

[51] Int. Cl.[7] .................................................. G08B 17/10
[52] U.S. Cl. ........................ 340/632; 340/628; 340/693; 73/31.02
[58] Field of Search .................................... 340/632, 521, 340/577, 693, 628, 540; 73/23.42, 31.02; 364/497, 550

[56] References Cited

U.S. PATENT DOCUMENTS

| | | | |
|---|---|---|---|
| 4,119,950 | 10/1978 | Redding | 340/524 |
| 4,704,607 | 11/1987 | Teather et al. | 340/825.07 |
| 4,893,005 | 1/1990 | Stiebel | 250/221 |
| 4,920,263 | 4/1990 | Fimian et al. | 250/255 |
| 5,132,968 | 7/1992 | Cephus | 370/94.1 |
| 5,159,315 | 10/1992 | Schultz et al. | 340/539 |
| 5,235,190 | 8/1993 | Tucker et al. | 250/435 |
| 5,406,265 | 4/1995 | Trozzo et al. | 340/632 |
| 5,428,964 | 7/1995 | Lobdell | 62/176.6 |
| 5,650,770 | 7/1997 | Schlager et al. | 340/573 |
| 5,761,908 | 6/1998 | Oas et al. | 62/3.2 |
| 5,786,767 | 7/1998 | Severino | 340/628 |
| 5,786,768 | 7/1998 | Chan et al. | 340/632 |

FOREIGN PATENT DOCUMENTS

| | | |
|---|---|---|
| 0 448 360 | 3/1991 | European Pat. Off. . |
| 0 527 307 A2 | 6/1992 | European Pat. Off. . |
| 2 754 911 | 10/1996 | France . |

OTHER PUBLICATIONS

GZA Remediation, Inc. (by Stephen Venuti), Air Monitoring And Emissions Control Plan, Aug., 1994.

GZA GeoEnvironmental, Inc. (by Michele A. Vose), Final Submittal—Field Sampling Plan—Suil/Brook Remediation Phase—Norwood PCB Superfund Site, Jun., 1997.

*Primary Examiner*—Edward Lefkowitz
*Assistant Examiner*—Davetta W. Goins
*Attorney, Agent, or Firm*—Foley, Hoag & Eliot, LLP

[57] ABSTRACT

The invention provides systems for perimeter air quality monitoring that can establish background levels of target contaminants in ambient air prior to initiation of remedial activities. The systems can develop remedial action levels that are protective of the public health for dust and vapors at the remediation property, and can monitor and document fence line ambient air levels of target contaminants during remedial activities. Accordingly the systems and process allow for evaluation of the need for dust or vapor control measures to reduce airborne containment levels to below levels of concern.

16 Claims, 5 Drawing Sheets

SYSTEMS AND METHODS FOR FENCELINE AIR MONITORING OF AIRBORNE HAZARDOUS MATERIALS

FIELD OF THE INVENTION

The invention relates to systems and methods for monitoring airborne hazardous materials, and more particularly to systems and methods for reducing hazardous conditions at environmental remediation sites.

BACKGROUND OF THE INVENTION

The remediation of soil contaminated by hazardous materials is an important environmental goal. In particular, remediation of contaminated sites removes from the local community a source of hazardous waste, and reclaims that land for a beneficial use. Consequently, the process of remediation is an important and valuable tool for land management, and its use has grown substantially in the United States.

However, as beneficial as remediation is, the process itself has some inherent risks. In particular, hazardous materials are present at the remediation site, which, although dangerous in themselves, are often in a stable form and if left untouched present a low risk to the surrounding community. Remediation often requires the removal of the contaminated materials from the remediation site causing subsurface soils to be disturbed. These subsurface soils may contain any number of hazardous materials that are easily made airborne, including volatile and semi-volatile organic compounds (VOC and SVOC), such as benzene and polycyclic aromatic hydrocarbons (PAH). The release of VOCs and SVOCs from remediation sites provides a risk of toxicity to the surrounding community, and the disturbance of soil containing these materials can cause ambient air quality to degrade substantially. Once released to the ambient air, these compounds are free to move away from the remediation site and into the local community based on prevailing meteorological conditions.

Although systems exist today for measuring air quality, these systems are generally just stand alone air sampling devices that typically are only employed once an air quality problem is suspected. Accordingly, these systems are generally reactionary, only providing information regarding the damage done.

Accordingly, it would be desirable to have a real time system for monitoring the quality of air leaving a remediation site to prevent or reduce public health risks to surrounding communities associated with on-site activities.

SUMMARY OF THE INVENTION

The invention provides systems for perimeter air quality monitoring that can establish background levels of target contaminants in ambient air prior to initiation of remedial activities. The systems can develop remedial action levels that are protective of the public health for dust and vapors at the remediation property, and can monitor and document fence line ambient air levels of target contaminants during remedial activities. Accordingly the systems and process allow for evaluation of the need for dust or vapor control measures to reduce airborne containment levels to below levels of concern.

To this end, the systems and methods described herein can include apparatus for monitoring airborne hazardous materials that includes a gas detector for analyzing an air sample to detect volatile organic compounds and a dust detector for detecting airborne particulate matter. The systems can also include a data communications device that couples to the gas detector and to the dust detector and that is capable of transmitting data signals over a data network. The apparatus can also include a gas processing instrument that is capable of identifying the types of volatile organic compound present in an air sample. The systems can further comprise an alarm that will generate an external notification signal which is representative of a volatile organic compound being at a concentration above a designated concentration level. Similarly, the systems described herein can also include an alarm for generating an external notification signal when dust levels have been detected above a concentration level that is acceptable to public health.

In one embodiment, the systems are programable such that an operator can select the individual volatile organic compounds that are being identified, monitored, or detected by the systems described herein. In a further embodiment, the systems can include controllers that are coupled to data communication devices and that allow for the access and control of the monitoring systems from a remote location.

The systems described herein can further comprise mechanisms for designating a threshold concentration of a selected volatile organic compound which is representative of a protective human health risk based concentration. Similarly, the systems include mechanisms for designating a threshold concentration of a dust material which is representative of a human health risk based concentration. The systems described herein can include weather-tight housings for enclosing the elements of the system and for providing an interior chamber that has a controlled interior environment.

In a further embodiment, the invention provides systems for monitoring airborne hazardous material that include a plurality of air monitoring stations that can be located around the perimeter of a remediation site. Each of the air monitoring stations can include a gas detector for analyzing an air sample to detect volatile organic compounds, a dust detector for detecting airborne particulate matter, and a data communications device coupled to the gas detector and to the dust detector and being capable of transmitting data signals over a data network. These systems can further include a data processor which is in communication with each of the data communication devices of the plural monitoring stations. The data processor can act and operate to control and monitor the stations and to compare the information received from these monitoring stations. The apparatus can also include a detector for generating a signal that is representative of wind direction across the site being monitored. These systems can also include a site contribution processor that is coupled to the detector, a gas detector and a dust detector for generating a signal representative of airborne hazardous materials generated at the site being monitored.

These systems can also include an alarm for generating a warning signal representative of a warning to begin vapor and or dust suppression controls to reduce airborne hazardous materials levels.

In another aspect, the invention can be understood as processes for monitoring airborne concentrations of volatile compounds and dust around a site. These processes can comprise the acts of providing a plurality of monitoring stations, each having a gas detector, a dust detector and a data communications device and a data processor, locating the monitoring stations around the perimeter of the site being remediated, sampling concentrations of volatile organic compounds and dust at each monitoring station, communicating the sampling information through the data communication device to the data processor and operating the data processor to compare sampling information to acceptable concentrations of total volatile organic compounds, individual volatile organic compounds and dust. These processes can also include the step of providing a detector for determining wind direction at the site being monitored and determining an upwind monitoring station and a downwind monitoring station, and processing sample information from the upwind monitoring and sampling information from the downwind monitoring station to determine a concentration of airborne particulate matter contributed from the site.

Other objects of the invention will, in part, be obvious, and, in part, be shown from the following description of the systems and methods shown herein.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION OF THE ILLUSTRATED EMBODIMENTS

To provide an overall understanding of the invention, certain illustrative embodiments will now be described, including a system for monitoring air quality at a remediation site. However, it will be understood by one of ordinary skill in the art that the systems and processes described herein can be adapted and modified to provide systems that can be employed to monitor air quality, water quality, or soil quality, or for any other suitable application as well as to provide systems for use at any type of site in need of monitoring. Other additions and modifications can be made to the invention without departing from the scope hereof.

Figure 1:
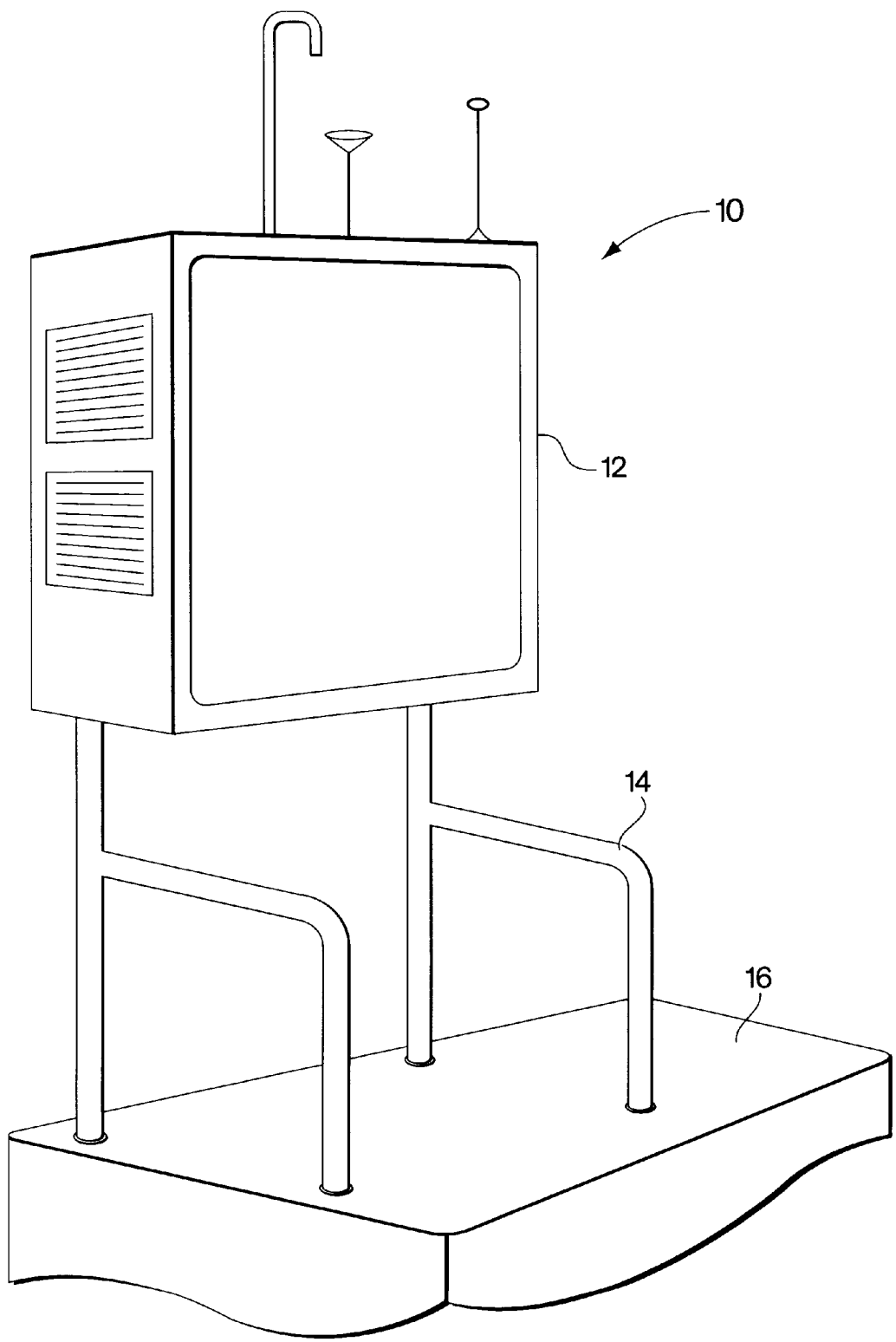
FIG. 1 depicts an air monitoring station for monitoring airborne hazardous materials.

FIG. 1 depicts one air monitoring station 10 that provides for monitoring airborne hazardous material. The air monitoring station 10 depicted in FIG. 1 includes a cabinet 12 mounted to a base 14. The cabinet 12 depicted in FIG. 1 is approximately three feet high by four feet wide and one foot deep. The cabinet 12 stands on a base formed from an iron pipe fixture that is connected to a cement base 16. The air monitoring station 10 is approximately seven to eight feet tall. The cabinets 12 and base 14 are adapted to withstand exposure to normal and severe weather conditions, allowing the air monitoring station 10 to be maintained outdoors for a prolonged period of time. Accordingly, the air monitoring station 10 can act as a permanent, or near permanent, sentry for monitoring for airborne hazardous material and can be part of a containment system capable of sounding an alarm upon the detection of airborne hazardous materials representative of a public health risk. To that end, the air monitoring station can provide for sounding a siren that instructs a remediation crew to take preventive measures to contain or curtail the production of airborne hazardous materials. Moreover, the air monitoring system 10 can be employed as part of a system for generating a database of air sample data to maintain a record of air quality during remediation activities.

Figure 2:
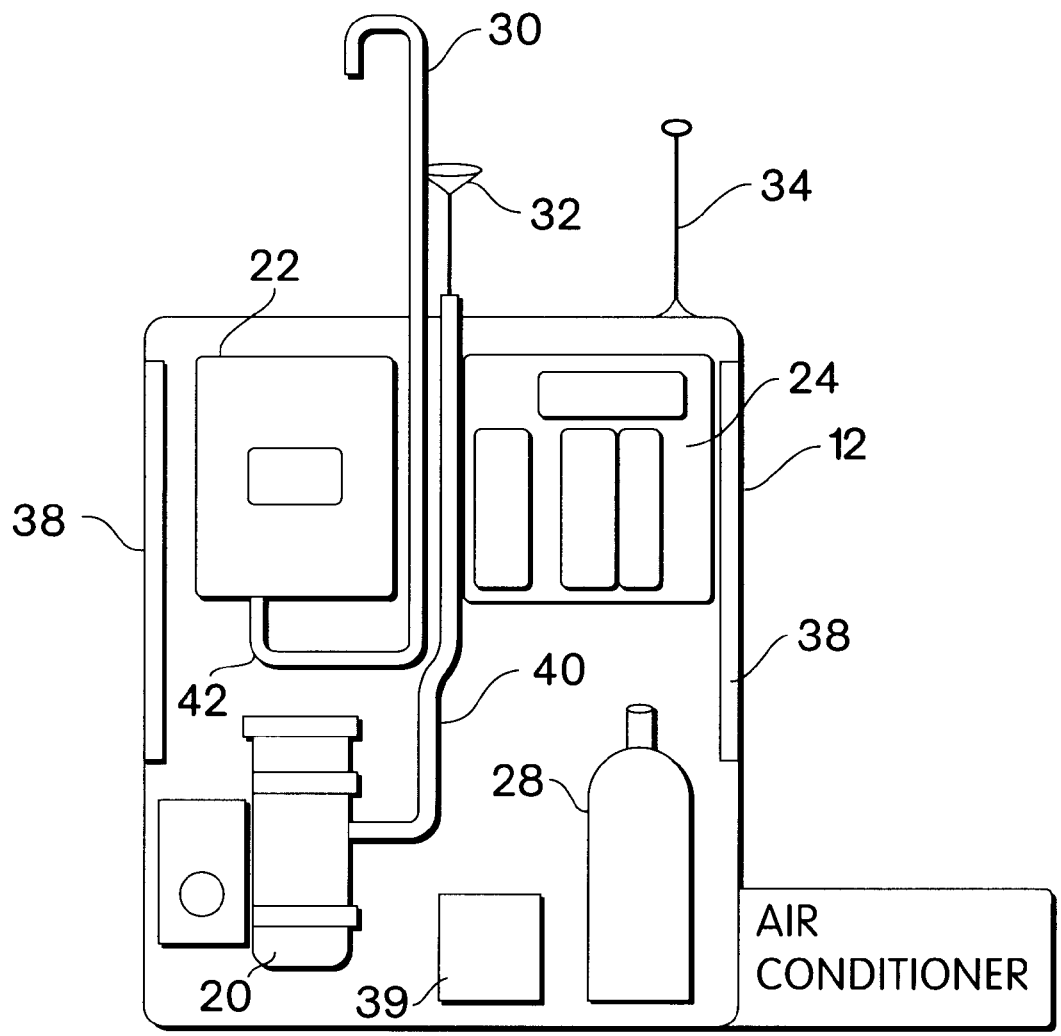
FIG. 2 depicts the internal components of the air monitoring station depicted in FIG. 1.

FIG. 2 depicts the components of the air monitoring station 10 that are maintained within the housing 12. Specifically, FIG. 2 depicts that the housing 12 contains a dust detector 20, a gas analyzer 22, a data communication device 24, and a reservoir of carrier gas 28. FIG. 2 further depicts that the housing 12 has mounted thereto a gas sampling inlet 30, a dust sampling inlet 32, and an antenna 34. Maintained within the housing 12, for controlling the environment therein, are heat exchanger elements 38, and a heater element 39. As shown in FIG. 2, the depicted housing 12 has a heat exchanger 38 mounted on either side of the housing 12. The housing 12 depicted in FIG. 1 is a weather-tight housing, and preferably is a NEMA-4 type housing suitable for providing a weathertight housing resistance to the elements and capable of protecting the components of the air monitoring station 10 from exposure to the external environment. As can be seen from FIG. 2, the housing 12 contains those heating and air conditioning devices necessary to maintain the interior compartment of housing 12 at selected environmental conditions. This is understood to provide the instrumentation, such as the gas analyzer 22, with a controlled operatiang environment, thereby reducing the likelihood that environmental conditions will influence the operation of the instrumentation. To this end, as will be understood from the description below, the environmental control devices, such as the heat exchanger gas, can be monitored and controlled from a central station, thereby allowing repair or adjustment if necessary. It will be understood that the depicted devices are provided for illustrative purposes, and that other devices and arrangements of devices can be employed without departing from the scope of the invention.

FIG. 2 further depicts that the housing 12 includes a dust detector element 20. The dust detector 20 monitors respirable dust levels as a surrogate for monitoring SVOCs such as PAHs. As is known in the art, surrogate monitoring provides a technique for estimating the concentration level of certain chemicals by examining the concentration level of a measurable surrogate and estimating, such as from soil samples, the percentage of that surrogate that is composed of the chemical being monitored. Although the systems described herein employ dust as a surrogate for PAH levels, any other surrogate detection method can be employed, with the selected method typically being chosen for being the optimal technique for the material being detected or for the given site conditions. The dust detector element 20 can be a light scattering particulate matter detector, and more particularly can be an infrared electromagnetic particle detector. One such infrared particle detector is manufactured and sold by the MIE Company of Billerica, Mass. As further shown by FIG. 2, the particle detector 20 couples by tubular elements 40 to the air sampling tube 32. The air sampling tube 32 extends out of the housing 12 and is capable of collecting an air sample that can be carried through tube 40 to the dust detector 20. The dust detector 20 can then operate as normal on the collected air sample to determine the concentration level of particulate matter in the air around the air monitoring station 10. The concentration level of particulate matter can be employed to estimate the concentration level of PAHs, or other chemical, in the air sample.

FIG. 2 further depicts that the housing 12 can contain a gas detector for analyzing an air sample to detect volatile organic compounds. In the embodiment depicted in FIG. 2 the gas detector 22 includes a gas chromatograph of the type manufactured and sold by PE Photovac of Norwalk, Conn. The gas chromatograph 22 couples via tubing 42 to the air sampling tube 30 that extends outwardly from the housing 12. The dust sampling inlet 30 can collect air samples from the ambient environment and provide the air samples through tube 42 to the gas chromatograph 22. There the gas chromatograph 22 can operate as normal to determine the concentration of volatile organic compounds in the environment ambient to the air monitoring station 10.

FIG. 2 further depicts that the housing 12 contains a data communications device 24. In the depicted embodiment the data communications device 24 is a radio of the type manufactured by the Motorola Company of Austin, Texas. The radio 24 couples to the antenna 34 for broadcasting via a radio link information signals to a central processing station (not shown) that can be employed for monitoring the sampling data generated at the air monitoring station 10. To this end, both the gas detector 22 and the dust detector 20 can couple to the data communication device 24 to provide the data communication device 24 with air sampling information. The data communication device 22 can format the air sampling data into a format suitable for transmission via a data network and broadcast this data to the data network for further analysis and recording by the central data processing system. Although the data communication device 24 depicted in FIG. 2 is a radio frequency link device, it will be apparent to one of ordinary skill in the art that other communication devices are practicable with the present invention, including cable networks, infrared links, short haul modem link or any other type of communication links suitable for carrying data from a remote location to a central processing location.

A reservoir of carrier gas 28 is also maintained within the housing 12 and acts to provide a source of carrying gas for delivering a sample into the gas chromatograph. In one embodiment, the reservoir contains helium, although any other suitable gas or combination of gases can be employed. The carrier gas can be an ultra zero air gas which gives the gas chromatograph a carrier gas to allow air to move through the columns of the gas chromatograph.

In operation, the individual components of the air monitoring station 10 can operate to collect samples of air at the site of the air monitoring station 10 and to process those samples to determine the concentration levels of airborne hazardous material in the environment around the air monitoring station. More particularly, the gas detector 22 can, through the air sampling tube 30, collect an air sample and process the air sample to determine the concentration of volatile organic compounds in the air or around the air monitoring station. The gas detector 22 can be a programmable device that will allow a user to set a concentration level of VOCs that indicates a public health risk has been triggered. The dust detector 20 can continuously sample the air around the monitoring station 10 to estimate the concentration of SVOCs or other materials in the air. Data from both detectors 20 and 22 will be passed, through the data communications device 24 to the central processor to provide continuous real-time air quality data for the air around the monitoring station 10.

Figure 3:
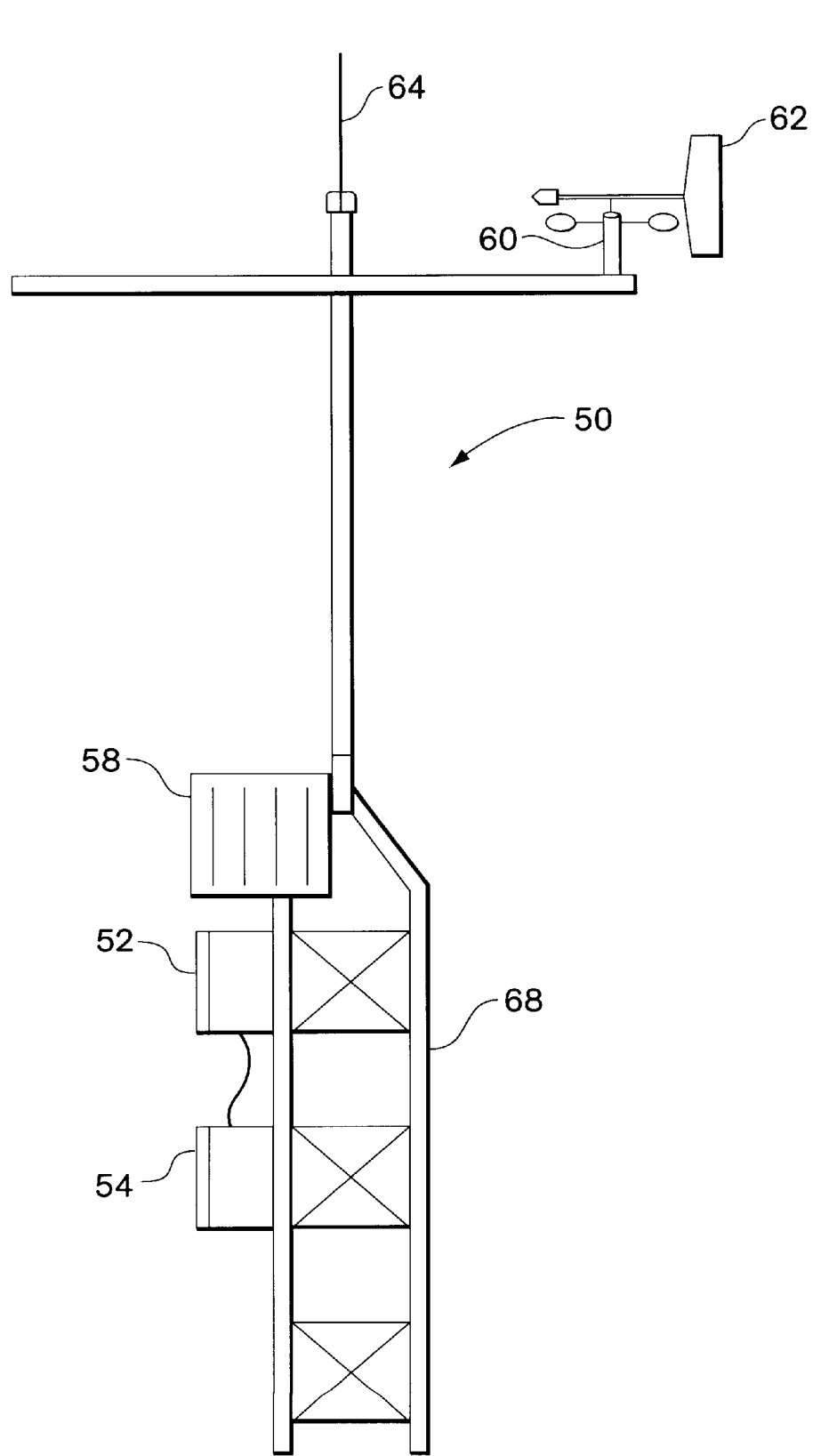
FIG. 3 depicts a weather monitoring station for use with the system of FIG. 1.

In cooperation with the air monitoring stations, the systems described herein can also include a weather monitoring station, such as the weather monitoring station depicted in FIG. 3. The weather monitoring station can collect information regarding atmospheric conditions including wind direction, wind speed, humidity, and any other meteorological condition relevant to an analysis of concentration levels of airborne materials. FIG. 3 depicts more specifically a weather station 50 that includes a weather processor unit 52, a data communication device 54, a solar cell panel 58, a wind speed meter 60, a vane 62, an antenna 64, and the base 68. The weather station 50 is designed to be maintained outdoors and therefore the electrical components are maintained within weathertight housings. The weather station 50 depicted in FIG. 3 is approximately 14 feet high and is assembled from components that are commercially available.

In particular, the wind speed meter 60, and weather vane 62 can be any commercially available components suitable for measuring wind speed and wind direction. The weather processor 52 depicted in FIG. 3 can be any suitable meteorological data such as the type sold by Campbell Scientific, Inc., under the name of MET DataOne. The data communication device 54 can be a radio frequency communication device, such as the data communication device 24 employed by the air monitoring system 10.

The components of the weather station 50 are interconnected such that the processor 52 can receive power from the solar cell panel 58. The processor 52 is a data processing unit that connects with the various measuring elements such as the vane 62 and wind speed meter 60. Other elements such as a barometer, humidity detector, or any other suitable meteorological measuring device can also be interconnected to the processor 52. The processor 52 collects the information and creates a data package that can include information representative of the time at which the data was collected. This information can be transferred via an electrical communication link to the data communication device 54. The data communication device 54 then can connect to the data network which can transmit data to the central data processing unit. In this way, information representative of the meteorological conditions at the remediation site can be maintained and detected by the central data processing unit.

The weather station 50 and the air monitoring station 10 can cooperate to provide fence line monitoring of air quality at a remediation site. For example, in one practice a plurality of air monitoring stations 10 are located around the perimeter of a remediation site, such as at locations that correspond to major compass headings. The weather station 50 can be centrally located at the site, or placed at the location most suited for measuring site weather conditions. Optionally, several weather stations can be employed. The air monitoring stations and weather station provide a continuous stream of real-time air quality data and environmental conditions to a control data processor. The control data processor can employ this information for monitoring air quality along the full perimeter of the remediation site.

Figure 4:
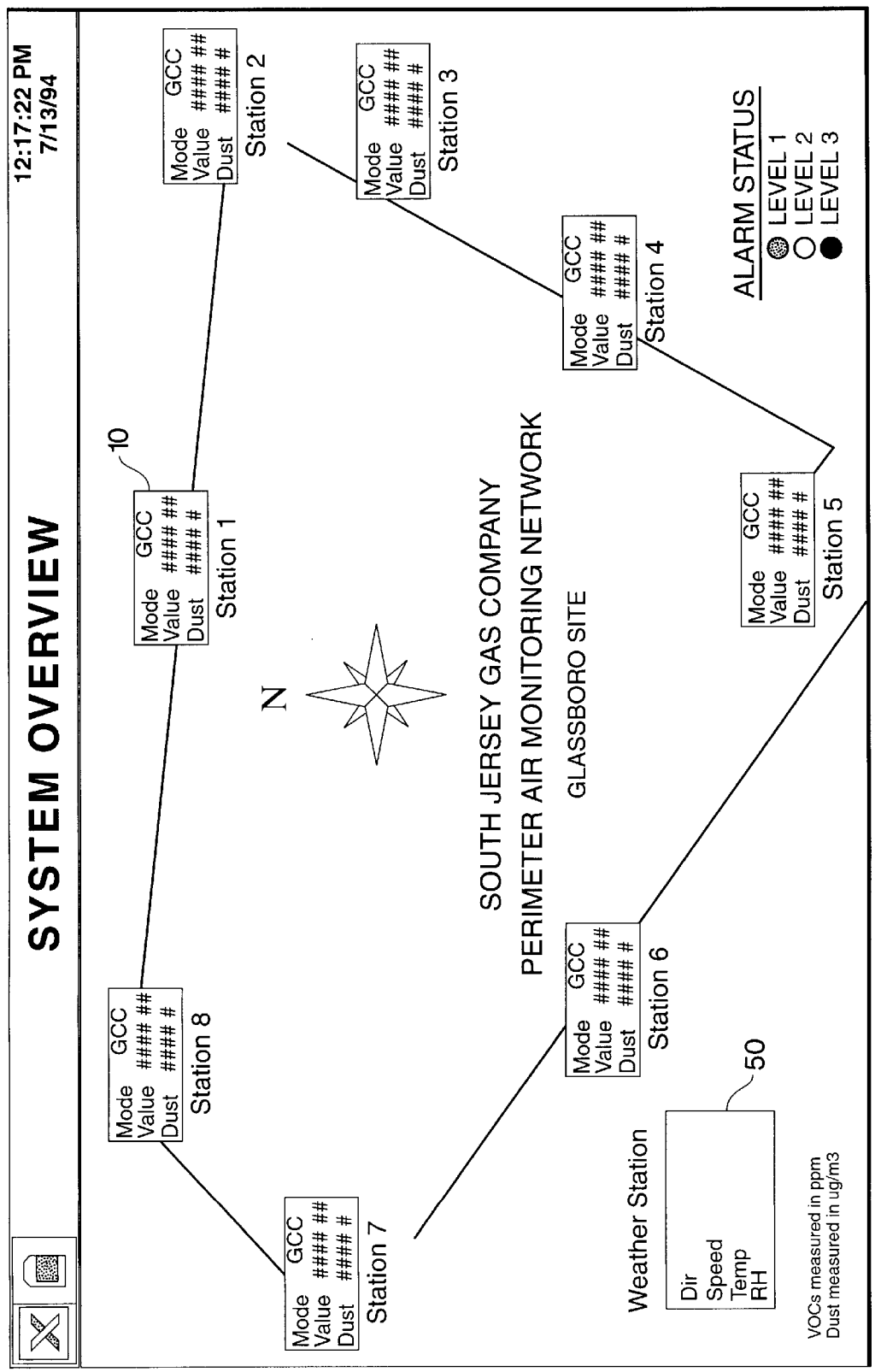
FIG. 4 depicts a system for monitoring air borne hazardous materials that includes a plurality of stations such as those depicted in FIG. 1.

FIG. 4 depicts a graphical representation of one such system for monitoring the air quality about the full perimeter of a remediation site. Specifically, FIG. 4 is a screen shot of a computer program operating on the central processing unit that monitors the air monitoring stations and weather station described above. FIG. 4 shows that a plurality of air monitoring stations are placed around the perimeter of the remediation site. It should be apparent that in other embodiments of the invention, the system can employ more or less air monitoring stations as well as more or less weather monitoring stations. Furthermore, in other embodiments of the invention, air monitoring stations can be placed at locations other than at the perimeter, including at locations that are remote from the remediation site but, perhaps are sites of acute interest, such as a local elementary school, a daycare center or a hospital.

An operator at the central processing unit can monitor each of the air monitoring stations and the weather station to see the status of the air quality at that particular location. To this end, the display provides to the operator a functional block representation of each of the air monitoring stations at the site, wherein the functional block contains information such as the mode of operation, the concentration level of the VOCs measured by that station, and the concentration level of dust measured at that station. Similarly, a functional block is provided to represent the weather station 50. The weather station functional block provides information representative of the wind direction, wind speed, the ambient air temperature and the relative humidity. All the information displayed by the central processor to the operator can be stored in a database to maintain a real-time record of the air quality and weather conditions at the perimeter of the remediation site. This database of information can be reviewed at a later date to demonstrate that unacceptable levels of hazardous materials did not pass over the perimeter of a remediation site and into the local community.

The display depicted in FIG. 4 further includes an alarm status block that indicates the relative alarm levels under which any remediation activity is partaking. The alarm status information includes a level one, level two and level three indicator. The level one indicator designates an "all clear" statement representative of the fact that the system detects no unacceptable risk to public health created by activity at the remediation site. A level two indicator represents a "caution" signal that indicates remediation activity may be rising to a level of concern for the public health. A level three indicator represents an "alert" signal that represents the detection of unhealthful concentrations of hazardous materials passing over the perimeter of the remediation site. A level three alarm warning can cause the central processor to sound a siren, or other type of physical alarm, or external notification that is broadcast to workers at the site. This alarm signal directs the workers at the site to take containment steps in order to reduce the flow of hazardous material past the perimeter of the remediation site. These steps can include: stopping all work, including excavating; laying down a protective foam over all newly exposed subsurfaces; or any other suitable containment step. Optionally, the external notification can be transmitted local community to officials.

Figure 5:
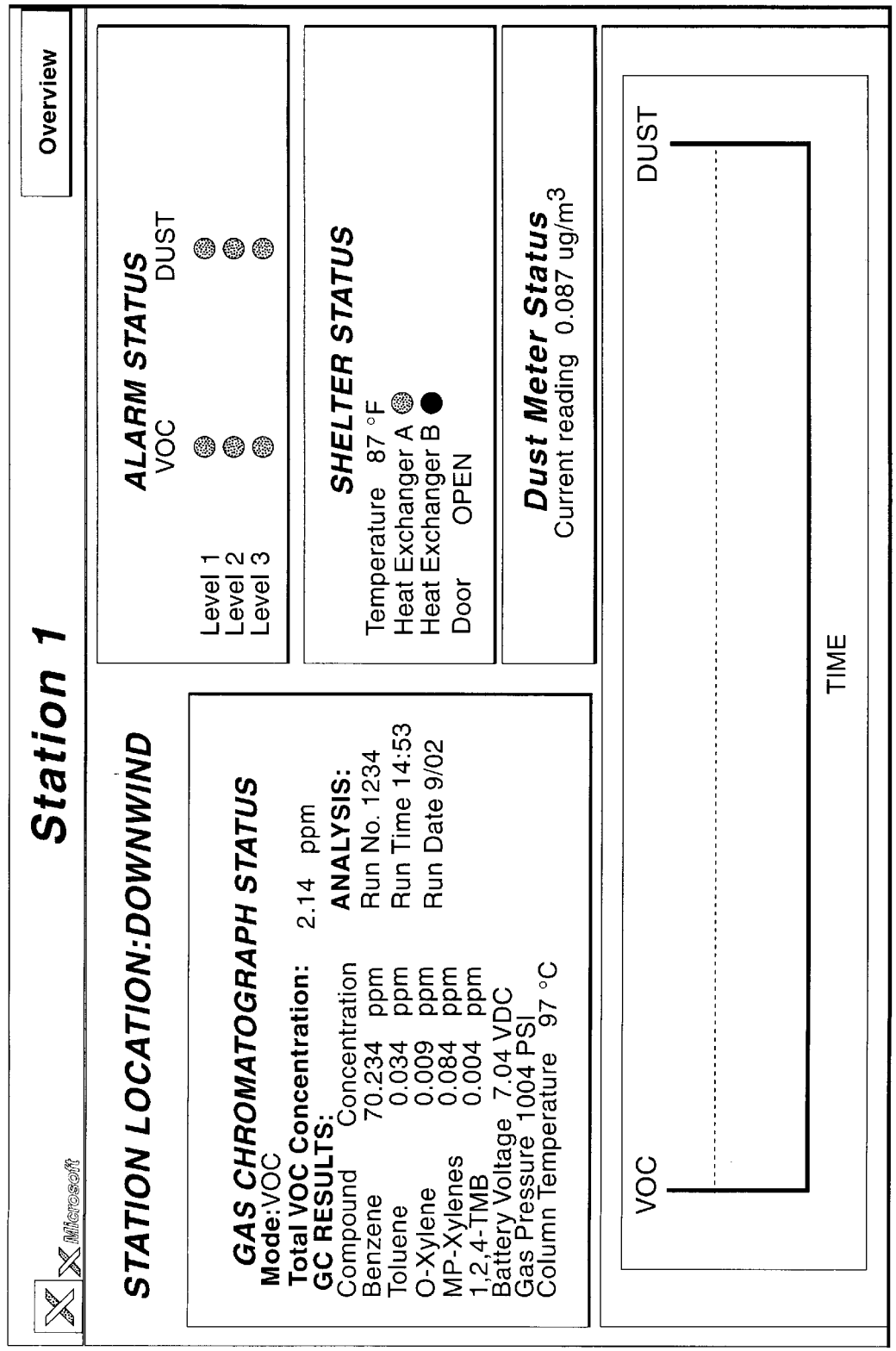
FIG. 5 depicts a screen of a computer system providing remote monitoring and control of the system of FIG. 3.

The alarm status indicated in FIG. 4 arises from any of the air monitoring stations indicating an unacceptably high level of concentration of hazardous material passing the perimeter of the remediation site. To determine more accurately the cause of the alarm, an operator at the central processing site can direct the central processing unit to display information representative of air monitoring conditions at each of the specific sites. FIG. 5 depicts a screen shot representing a display that shows the air sample data collected at one particular site. Specifically FIG. 5 shows an alarm status specific to the particular station, in this case station one. FIG. 5 further depicts that the gas detector, in this case a gas chromatograph. As shown in FIG. 5, the gas chromatograph can report in the mode in which the gas chromatograph is operating. In this embodiment, the mode is set as "VOC" reprenting a mode of operation in which volatile organic compounds are being detected. The gas chromatorgraph status also includes a report of the total VOC concentration. If the total VOC concentration is above an acceptable level of VOCs, the gas chromatograph can switch into an analyze and identify mode in which the air sample is analyzed to determine to the receive concentrations of certain selected compounds. FIG. 5 depicts one embodiment wherein the GC analyzes the air sample to determine the concentration of benzene, toluene as well as other particular VOCs that are of interest at that remediation site. The gas chromatograph also reports internal status regarding the instruments' operations. This could include information regarding the gas pressure and column temperature as well as the battery voltage. The gas chromatograph also reports information that identifies the run under which the results are performed. This can include a run number, a time at which the run was performed and the date on which the run is performed. FIG. 5 also depicts that each individual station can report information regarding the internal environment of the air monitoring station. This internal environment information can include the temperature, the operational status of the heat exchangers, and whether the door is open or closed on the air monitoring station. FIG. 5 further depicts that the dust meter can report information regarding the relative concentration of dust in the air at the site of the air monitoring station. Finally, the air monitoring station can include a graphic that shows the relative concentrations of the dust and the VOCs being detected over time by the air monitoring station.

FIG. 5 also shows that the air monitoring station indicates the wind direction at the monitoring station. By monitoring wind direction, the central processor can tell whether or not the air monitoring station reporting unacceptably high concentration levels is upwind or downwind of the remediation site. This allows the central processing station to determine in which direction airborne hazardous materials are traveling. Moreover, this also allows the central processing unit to determine whether or not the unacceptably high levels of airborne hazardous materials arises from activities at the remediation site. Specifically, the central processing system can select an upwind monitoring station and a downwind monitoring station. The relative concentrations of particulate matter between the upwind station and the downwind station can be compared. In this way, it can be determined whether or not air quality has been affected by activity at the remediation site, or whether or not air being carried into the remediation site is already sufficiently contaminated to be deemed unhealthful. In one step, the relative concentration level of VOCs from the upwind location is compared to the relative concentration level of VOCs at the downward concentration level, particularly by subtracting the two numbers. The difference between the two concentration levels is understood as the site contribution to VOCs in the environment. Based on this differential information, the remediation site can determine whether or not containment activities at the remediation site could be effective in improving air quality downwind of the remediation site.

The above described embodiments are merely illustrative of the systems and methods ofthe invention, and other systems and methods, such as systems for monitoring air quality at a chemical plant or for monitoring air quality moving into an enclosed area. Accordingly, it will be understood that the invention is not to be limited to the embodiments disclosed herein, but is to be understood from the following claims, which are to be interpreted as broadly as allowed under the law.

I claim:

1. An apparatus for monitoring air borne hazardous materials at more than one location and for comparing information from different locations, comprising a plurality of monitoring stations located around the perimeter of a site for monitoring air borne hazardous materials, each said monitoring station having a gas detector for analyzing an air sample to detect volatile organic compounds, a dust detector for detecting air borne particulate matter, and a data communications device coupled to the gas detector and to the dust detector and being capable of transmitting data signals over a data network, and a data processor in communication with each said data communications device, for controlling the monitoring stations and comparing the information received from the monitoring stations.

2. An apparatus according to claim 1, further including a detector for generating a signal representative of wind direction across a site being monitored.

3. An apparatus according to claim 2, further including a site contribution processor coupled to said detector, said gas detector and said dust detector for generating a signal representative of airborne hazardous material generated at the site being monitored.

4. An apparatus according to claim 1, further including an alarm for generating a containment warning signal representative of a warning to begin containment of airborne hazardous materials.

5. An apparatus according to claim 1, further including instrumentation for identifying individual volatile organic compounds for detection.

6. An apparatus according to claim 1, further including a user interface for allowing an operator to designate a threshold concentration for a selected volatile organic compound.

7. An apparatus according to claim 1, further including a mechanism for designating a threshold concentration of total volatile organic compounds.

8. An apparatus according to claim 1, further including a user interface for allowing an operator to designate a threshold concentration of dust.

9. A process for monitoring air borne concentrations of volatile organic compounds and dust around a site, comprising (a) providing a plurality of monitoring stations, each having a gas detector for analyzing an air sample to detect volatile organic compounds, a dust detector for detecting air borne particulate matter, and a data communications device coupled to the gas detector and to the dust detector and being capable of transmitting data signals over a data network, and a data processor in communication with each said data communications device, for controlling the monitoring stations and comparing the information received from the monitoring stations.

(b) locating the monitoring stations around the perimeter of the site, (c) sampling concentrations of volatile organic compounds and dust at each monitoring station, (d) communicating this sampling information through the data communications device to the data processor, and (e) operating the data processor to compare sampling information to threshold concentrations of total volatile organic compounds, individual volatile organic compounds, and dust.

10. A process according to claim 9, further comprising providing a detector for determining wind direction at a site being monitored, determining an upwind monitoring station and a downwind monitoring station, and processing sampling information from said upwind monitoring station and sampling information from said downwind monitoring station to determine a concentration of airborne particulate material contributed from the site being monitored.

11. A process according to claim 9, further comprising providing an alarm for generating, in response to a detected concentration of airborne particulate material, a containment signal representative of an instruction to contain airborne particulate material generated at the site being monitored.

12. A system for monitoring airborne hazardous material, comprising a data processor coupled to a data network, the data processor configured to monitor air quality at a site; and a plurality of monitoring stations located around a perimeter of the site, each monitoring station including:

a weather tight housing having an environmental control unit for monitoring an interior chamber of the housing and for maintaining the interior chamber at a selected environmental condition, said interior chamber containing a gas detector for analyzing an air sample to detect volatile organic compounds, a dust detector for analyzing an air sample to detect airborne particulate matter, and a data communications device coupled to the gas detector, the dust detector and the control unit and being capable of transmitting data signals over the data network representative of sampling information generated from the gas detector and the dust detector and environmental information generated from the control unit.

13. A system according to claim 12, further including an environmental controller coupled to the data communications device for selectively controlling an environmental characteristic of the interior chamber.

14. A system for monitoring contamination at a remediation site, comprising a plurality of air sampling devices each capable of detecting a hazardous airborne material within an air sample and each being located about the periphery of the remediation site, a data network coupled to each of said plural air sampling devices and being capable of transferring data signals, a data processing system coupled to said data network for communicating with said plural air sampling devices and for collecting sampling data representative of a detected presence of a hazardous airborne material, and for storing said sampling data in a data storage unit, whereby a database of sampling data can be collected.

15. A process for providing a perimeter air monitoring service, comprising selecting locations about the periphery of a remediation site for a plurality of air sampling devices each capable of detecting a hazardous airborne material within an air sample, placing the plurality of air sampling devices at the selected locations, measuring environmental conditions at the remediation site, providing a data network coupled to each of said plural air sampling devices and being capable of transferring data signals, and operating a data processing system coupled to said data network for collecting sampling data representative of a detected presence of a hazardous airborne material, for collecting data representative of measured environmental conditions at the remediation site and processing the sampling data and the environmental data to determine the presence of airborne contaminants traveling past the perimeter of the remediation site.

16. The process of claim 15 further comprising operating the data processing system to distinguish hazardous airborne material generated by the remediation site from other hazardous airborne material entering the remediation site from about the periphery of the remediation site.

* * * * *